United States Patent [19]

Miller

[11] Patent Number: 4,861,719
[45] Date of Patent: Aug. 29, 1989

[54] DNA CONSTRUCTS FOR RETROVIRUS PACKAGING CELL LINES

[75] Inventor: A. Dusty Miller, Seattle, Wash.

[73] Assignee: Fred Hutchinson Cancer Research Center, Seattle, Wash.

[21] Appl. No.: 856,672

[22] Filed: Apr. 25, 1986

[51] Int. Cl.[4] .................. C12N 7/04; C12N 15/00; C12N 5/00; C12R 1/91

[52] U.S. Cl. .................. 435/236; 435/68; 435/91; 435/172.3; 435/240.2; 435/320; 435/948; 536/27; 935/32; 935/34; 935/57; 935/70; 935/71

[58] Field of Search .................. 435/91, 172.1, 172.3, 435/236, 239, 240.2, 320, 948; 935/6, 22, 32, 34, 57, 60, 62, 63, 70, 71, 79; 536/27

[56] References Cited

U.S. PATENT DOCUMENTS 4,650,764  3/1987  Temin et al. .................. 435/240

OTHER PUBLICATIONS

Mann, R., R. C. Mulligan, and D. Baltimore, 1983, Construction of a Retrovirus Packaging Mutant and Its Use to Produce Helper-Free Defective Retrovirus, Cell, 33:153-159.

Watanabe, S., and H. M. Temin, 1983, Construction of a Helper Cell Line for Avian Reticuloendotheliosis Virus Cloning Vectors, Mol. Cell. Biol., 3:2241-2249.

Shank, P. R., and M. Linial, 1980, Avian Oncovirus Mutant (SE21Qlb) Deficient in Genomic RNA: Characterization of a Deletion in the Provirus, J. Virol, 36:450-456.

Cone, R. D., and R. C. Mulligan, 1984, High-Efficiency Gene Transfer into Mammalian Cells: Generation of Helper-Free Recombinant Retrovirus with Broad Mammalian Host Range, Proc. Natl. Acad. Sci. USA, 81:6349-6353.

Miller, A. D., M. F. Law, and I. M. Verma, 1985, Generation of Helper-Free Amphotropic Retroviruses that Transduce a Dominant-Acting Methotrexate-Resistant DHFR Gene, Mol. Cell. Biol., 5:431-437.

Sorge, J., D. Wright, V. D. Erdman, and A. E. Cutting, 1984, Amphotropic Retrovirus Vector System for Human Cell Gene Transfer, Mol. Cell. Biol., 4:1730-1737.

Panganiban, A. T., and H. M. Temin, 1983, The Terminal Nucleotides of Retrovirus DNA are Required for Integration but not Virus Production, Nature, 306:155-160.

Mann, R., and D. Baltimore, 1985, Varying the Position of a Retrovirus Packaging Sequence Results in the Encapsidation of Both Unspliced and Spliced RNAs, J. Virol, 54:401-407.

*Primary Examiner*—Robin Teskin
*Assistant Examiner*—Richard C. Peet
*Attorney, Agent, or Firm*—Christensen, O'Connor, Johnson & Kindness

[57] ABSTRACT

DNA constructs consisting essentially of the promoter, gag, pol, and env sequences of a helper virus useful for making retrovirus packaging cell lines that do not yield helper virus and do not transfer the packaging function. Such DNA molecules are constructed by deleting from the genome of a replication-competent retrovirus all cis-acting elements except for the tRNA binding site. Specifically, deletion is made of the packaging signal, the site for initiation of second strand DNA synthesis, the site required for translation of reverse transcriptase during first strand DNA synthesis, and the provirus integration signal. DNA construct pPAM3 (ATCC No. 40234) is a representative embodiment. A cell line containing such an altered viral genome does not transmit this virus or transfer the packaging signal, but will transmit high titers of other viral RNAs containing the proper cis-acting elements, including retroviral vectors designed to carry foreign genes. Cell line PA317 (ATCC No. CLR 9078) is a representative embodiment.

11 Claims, 5 Drawing Sheets

DNA CONSTRUCTS FOR RETROVIRUS PACKAGING CELL LINES

This invention was made partly with Government support under grant CA41455 awarded by the National Cancer Institutes. The Government has certain rights in the invention.

FIELD OF THE INVENTION

This invention relates to the field of genetic engineering and more particularly to DNA constructs useful for making retrovirus packaging cell lines that can be used to produce retrovirus vectors, but that do not yield helper virus and do not transfer the packaging function.

BACKGROUND OF THE INVENTION

Referring to FIG. 1, some pertinent features of the retroviral life cycle are depicted. The infectious retroviral agent is called a virion. Envelope glycoprotein on the surface of the virion recognizes receptors that mediate entry (1) of two copies of the retroviral genome, each an RNA molecule of between about 8,000 and 10,000 nucleotides, into a target cell. The two genomic virion RNA molecules are copied (2) by a viral reverse transcriptase enzyme into duplex linear and circular, supercoiled viral DNA (v-DNA) molecules. The virion RNA first serves as a template for the transcription of a complementary DNA nucleotide sequence (minus strand), and a second-strand DNA copy (plus strand) is then made using the reverse transcribed minus-strand DNA as a template.

Although unintegrated v-DNA can be transcribed (dashed arrow), some of the circular DNA molecules integrate (3) into the cellular genome at a precise point on the viral DNA molecule and a random, or near random, site on host chromosomal DNA. The integrated viral DNA copy is called a provirus.

The pertinent structural elements of a typical provirus are depicted in FIG. 2. Long terminal repeats (LTRs) containing sequences copied from both ends of viral genomic RNA are located at each end of the DNA provirus and linked directly to host DNA. These LTRs contain regulatory sequences for the expression of the genes required for viral replication: gag, internal structural protein; pol, reverse transcriptase; and env, viral envelope glycoprotein. The LTR regulatory sequences include promoters for the initiation and signals for the termination of transcription. The LTRs usually also include powerful enhancer sequences which amplify the rate of transcription of the viral genes to the point that proviral RNA transcripts may comprise as much as 0.1 to 1% of total cellular messenger RNA. The transcriptional promoter/enhancer apparatus associated with some retroviruses appears to function only when introduced into particular cell types, resulting in a tissue specific expression of the viral genes.

Referring again to FIG. 1, the integrated provirus is transcribed (4) into both messenger RNA and full-length genomic virion RNA. The viral messenger RNA is expressed into viral proteins on cellular polysomes (5). The virion RNA contains specific sequences serving as packaging signals for virion assembly (6). Virion RNA and viral proteins are assembled into new virions which bud from the infected host cell. In completing their replicative process, retroviruses usually do not lyse the host cell, and so the retrovirus life cycle constitutes an efficient mechanism for the introduction and high level expression of genes in living host cells.

Some retroviruses can grow and reproduce only in the presence of another virus. The latter, so-called helper or replication-competent virus, by its infection of a cell, enables the former, so-called replication-defective virus, to multiply by supplying one or more functions or factors that the defective virus lacks.

Retroviruses are becoming important tools for efficient transfer of genes into eukaryotic cells, due in large measure to the availability of retrovirus packaging cell lines which allow production of infectious but replication-defective retrovirus vectors in the absence of helper virus. Such vectors will infect and integrate into cells, but putatively cannot replicate and spread. These properties make possible a variety of studies where virus spread would make the interpretation of results difficult or impossible. An additional important use of retroviruses may be in human gene therapy, and viruses for clinical use must be helper free in order to avoid helper-induced disease or virus spread outside of the treated patient.

Strategies for production of such virus have been described previously. Cell 33: 153-159, 1983; Mol.Cell.Biol. 3(12): 2241-2249, 1983. These techniques generally rely on packaging vectors which synthesize viral proteins from mRNAs that cannot themselves be packaged into virions. The phenomenon was first observed in a cell line containing a mutant avian sarcoma virus which shed viral particles lacking viral genomic RNA. However, several problems with prior retrovirus packaging lines have been recognized. Some have limited host range, while others produce only low titers of retroviral vectors.

Previous work has shown that a region between the 5' splice site and the initiator codon of the gag protein is required for efficient packaging of retroviral RNA into virions. Cell 33: 153-159, 1983; J.Virol. 36(2): 450-456, 1980. Deletion of this region, or packaging signal, has allowed construction of retrovirus packaging cell lines by several groups. Proc.Natl.Acad.USA 81: 6349-6353; Cell 33: 153-159, 1983; Mol.Cell.Biol. 5: 431-437, 1985; Mol.Cell.Biol. 4: 1730-1737, 1984.

Integration of the DNA form of the virus is catalyzed by a viral integrase which recognizes a joint formed between the ends of two LTRs, and deletion of this region reportedly prevents virus integration. Nature 306: 155-160, 1983.

A packaging cell line that contains a virus with deletions of the origin of second strand DNA synthesis as well as the packaging signal has been described, but vector titers from this line ($10^3$ cfu/ml) are reportedly low. Mol.Cell.Biol. 4: 1730-1737, 1984.

A packaging system with limited host range that is based on avian reticuloendotheliosis virus has also been described. Mol.Cell.Biol. 3: 2241-2248, 1983. The gag and pol proteins, and the env protein, are synthesized from separate DNA constructs. The packaging signal was also removed from the constructs. However, neither helper virus production nor packaging system transfer from this line were extensively analyzed.

Both of the high-titer, wide host range packaging cell lines currently available are nearly identical in construction, and rely on viral protein synthesis from a provirus almost identical with a helper virus except that the signal for packaging of viral RNA has been deleted. Proc.Natl.Acad.Sci.USA 81: 6349-6353, 1984; Mol.Cell.Biol. 5:431-437, 1985. Recently, however, low level transmission of a retroviral vector lacking a packaging signal has been reported. J.Virol. 54(2): 401–407, 1985.

SUMMARY OF THE INVENTION

The present invention is predicated on the discovery that available retrovirus packaging cell lines made with helper virus lacking the viral RNA packaging signal may not only transmit the deleted viral genome at low levels but may also allow recombination with some retroviral vectors leading to production of helper virus at high levels. Since retroviruses used in gene therapy must be helper free, such packaging cell lines are now recognized to be unsuitable for clinical applications. To solve this problem, systematic alterations in a replication-competent viral genome were made to effect maximum interference with cis-acting elements while preserving production of transacting factors. The requisite DNA construct was found to consist essentially of the promoter, gag, pol, and env sequences of a helper virus. Such a DNA molecule may be constructed by deleting from the genome of a replication-competent retrovirus all cis-acting elements except for the tRNA binding site. Specifically, deletion is made of the packaging signal, the site for initiation of second strand DNA synthesis, the site required for translation of reverse transcriptase during first strand DNA synthesis, and the provirus integration signal. DNA construct pPAM3 (ATCC No. 40234) is a representative embodiment. A cell line containing such an altered viral genome does not transmit this virus or transfer the packaging signal, but will transmit high titers of other viral RNAs containing the proper cis-acting elements, including retroviral vectors designed to carry foreign genes. Cell line PA317 (ATCC No. CRL 9078) is a representative embodiment.

DETAILED DESCRIPTION OF THE PREFERRED EMBODIMENT

Figure 1:
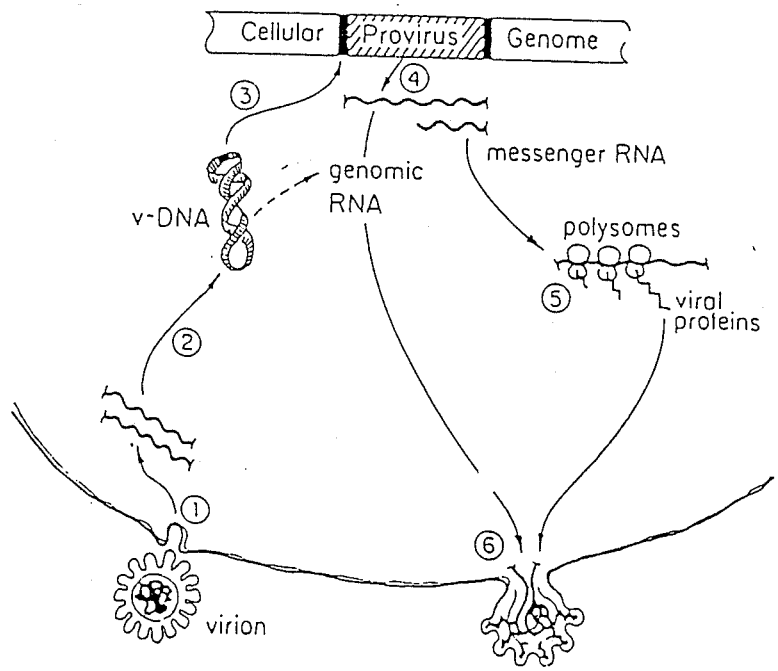
FIG. 1 (prior art) depicts some pertinent features of retroviral replication.
Figure 2:
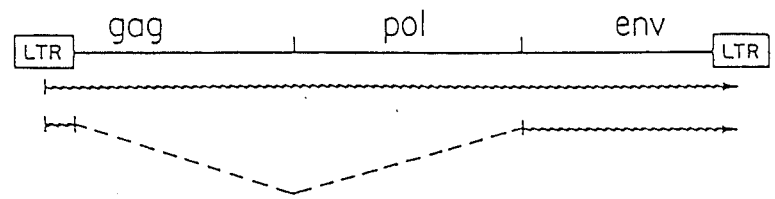
FIG. 2 (prior art) depicts some pertinent structural elements of a typical provirus.

Retrovirus packaging cell line PA317 (ATCC No. CRL9078) and packaging DNA construct pPAM3 (ATCC No. 40234) are on deposit at the American Type Culture Collection, 12301 Parklawn Drive, Rockville, MD 20852.

Elements required for retrovirus replication can be divided into cis- and trans-acting factors. The trans-acting factors include proteins encoded by the viral genome that are required for encapsidation of the viral RNA, entry of virions into cells, reverse transcription of the viral genome, and integration of the DNA form of the virus into host DNA. The cis-acting factors include signals present in the viral RNA which interact with these proteins and other factors during virus replication. Coffin, J., Genome Structure, pp. 17–74, in R. Weiss, N. Teich, H. Varmus, and J. Coffin (eds.), RNA Tumor Viruses, Vol. 2, Cold Spring Harbor Laboratory, Cold Spring Harbor, NY, 1985, hereby incorporated by reference.

In order to make a retrovirus packaging cell line with the lowest propensity for generating replication-competent virus, the genome of a replication-competent virus was systematically altered to maximally interfere with cis-acting elements while preserving production of trans-acting factors. A cell line containing the discovered altered viral genome does not transmit this virus, but will transmit other viral RNAs containing the proper cis-acting elements, including retroviral vectors designed to carry foreign genes.

As a model system, the replication-competent amphotropic retrovirus AM-MLV (pAM, see FIG. 3) was used for production of mutant viral genomes because of the broad host range of this virus, which is known to include mice, rats, chickens, cats, dogs, monkeys, and humans. The trans-acting factors encoded by this murine retrovirus include the gag and pol proteins, which are translated from the unspliced viral genome RNA, and the env protein, which is translated from a spliced message. Transcription of both mRNAs is driven by a strong promoter in the viral LTR. The primary translation products are cleaved by proteases to yield proteins involved in virus replication.

There are several steps at which transmission of replication-competent virus might conceivably be inhibited without affecting production of virion proteins. Deletion of the packaging signal has been employed. The construct pPAM (FIG. 3) was recently used to make such retrovirus packaging cell lines. Mol.Cell.Biol. 5: 431–437, 1985.

Further deletions were made to eliminate other cis-acting elements. Reverse transcription of the viral genome involves initiation of first strand DNA synthesis at a tRNA molecule that is noncovalently bound to the 5' end of the viral genome. Synthesis continues to the 5' terminus of the virus, where a jump to homologous sequences at the 3' end of the virus occurs, and the remainder of the first strand is synthesized. Second strand DNA synthesis starts at a point between the terminator codon of the env gene and the 3' LTR and proceeds in the 3' direction using the first strand DNA as a template. Deletions of sites in the virus involved in the above steps were made.

Figure 3:
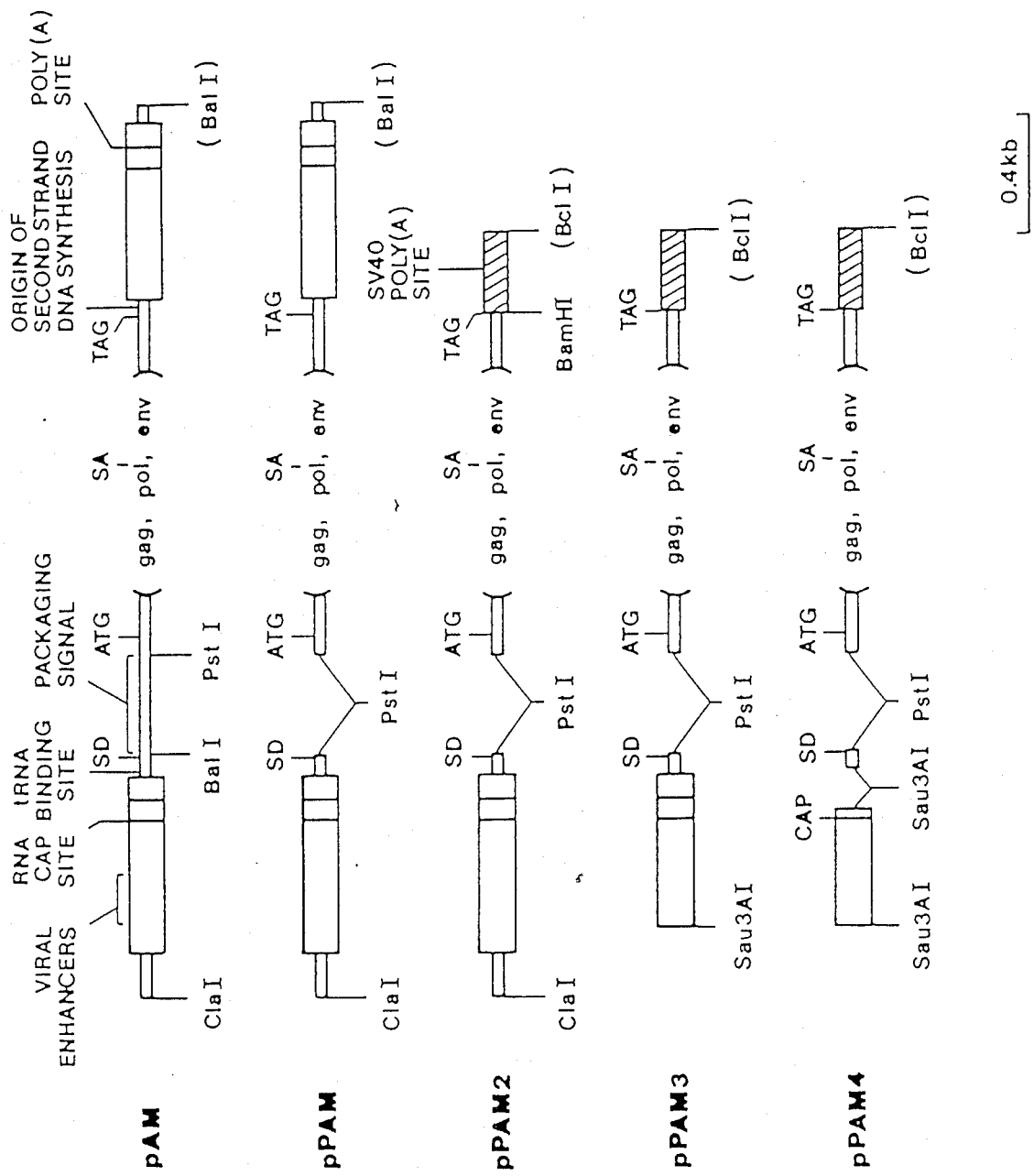
FIG. 3 depicts representative packaging DNA constructs as described in Example 3.

FIG. 3 depicts representative viral mutants with different combinations of deletions of cis-acting regions. In pPAM, the packaging signal has been removed. In pPAM2 the packaging signal and viral sequences 3' of the env protein terminator codon have been removed. The SV40 late region polyadenylation signal was added at the 3' end to provide for polyadenylation of viral mRNAs. The deletion at the 3' end of the virus removes the site for initiation of second strand DNA synthesis and the 3' R region that is required for translocation of reverse transcriptase during first strand DNA synthesis. In addition to these changes, pPAM3 has a deletion of the 5' of the 5' LTR, and thus a proper integration signal cannot be made from the remaining sequences. In pPAM4 all of the above deletions have been made, and in addition the 3' end of the 5' LTR and the tRNA primer binding site have been removed. The viral promoter and the splice donor used to make the env mRNA were left intact in pPAM4.

The deleted constructs were introduced into cells by cotransfection with a selectable marker to make various retrovirus packaging cell lines. Packaging cells made using the most heavily deleted construct, pPAM4, did not produce virus vectors at high titer. Packaging cell lines made using an intermediate construct, pPAM3, did produce virus vectors at high titer ($10^6$–$10^7$ cfu/ml). The packaging construct pPAM3 was made by deletion of the retrovirus packaging signal, all of the 3' LTR, part of the 5' LTR, and the site for second strand DNA synthesis. Thus RNA transcribed from pPAM3 should be inefficiently packaged into virions, and reverse transcription and integration of any resultant virus should be impossible. Indeed, no packaging function transfer from PA317 cells containing pPAM3 was detected. However, helper virus apparently arose in PA12 cells in the absence of any apparent source of contamination. Perhaps at very low frequency helper virus production can occur, possibly as a result of recombination of the packaging system with endogenous retroviris-like DNA or RNA elements found in mouse cells. This phenomenon should be significantly reduced in the new packaging cell lines described here.

Furthermore, helper virus production, a measured by $S+L^-$ assay, was observed for PA12 cells containing the Neo-virus pN2. Similarly, helper virus production from Psi-2 ecotropic retrovirus packaging cells (Cell 33: 153–159, 1983) was observed after introduction of the N2 vector. The Neo-virus N2 interacts with PA12 or Psi-2 packaging cells to yield helper virus at high frequency, presumably due to copackaging of the packaging system RNA and the Neo-virus RNA, followed by recombination in the common gag region during reverse transcription in an infected cell. This event appears to occur in the packaging cell populations, as clonal lines can be isolated that are initially helper-free, but that produce helper virus eventually. While cells infected with replication-competent virus are resistant to reinfection with virions having the same pseudotype, PA12 and Psi-2 cells are much less resistant (Somat.-Cell.Mol.Genet. 12: 175–183, 1986). Thus, infection and recombination between copackaged RNAs can occur in packaging cell lines containing helper virus lacking only the packaging sequence. In contrast, no helper virus production was detected from PA317 cells containing the N2 virus. A double recombination event would be required between the pPAM3 packaging system and the N2 virus in this system, which event must be quite rare. The N2 virus has characteristics which make it a useful vector. For instance, in canine and human marrow infections, only N2 and another virus containing gag sequences permitted efficient infection. The PA317 cell line now permits production of the N2 virus in the absence of helper virus, and this utility should extend to other potentially useful vectors which interact with previously available packaging cell lines to produce helper virus.

Retroviral vectors produced by PA317 cells can infect mouse, rat, cat, dog, and human cells, and thus have an amphotropic host range In particular, hemopoietic progenitor cells from human bone marrow have been infected using retroviral vectors secreted from PA317 cells. Mouse embryo cells have been similarly infected. Vector titer from the PA317 cells is also very high (up to $10^7$ cfu/ml), and so these cells should be useful for exploring potential human gene therapy.

The following Examples are presented to illustrate the advantages of the present invention and to assist one of ordinary skill in making and using the same. These Examples are not intended in any way to otherwise limit the scope of the disclosure or the protection granted by Letters Patent hereon.

EXAMPLE 1

Virus aassay.

Previously described cell lines include NIH/3T3 TK$^-$ (J.Virol. 39: 935–944, 1981), PA12 (Mol.Cell.Biol. 5: 431–437, 1985), Psi-2 (Cell 33: 153–159, 1983), and 208F (Virol. 98: 461–465, 1979). Cells were grown in Dulbecco modified Eagle medium with high glucose (4.5 g/l) supplemented with 10% calf serum (Psi-2 cells) or 10% fetal bovine serum (all other cell lines).

Figure 4:
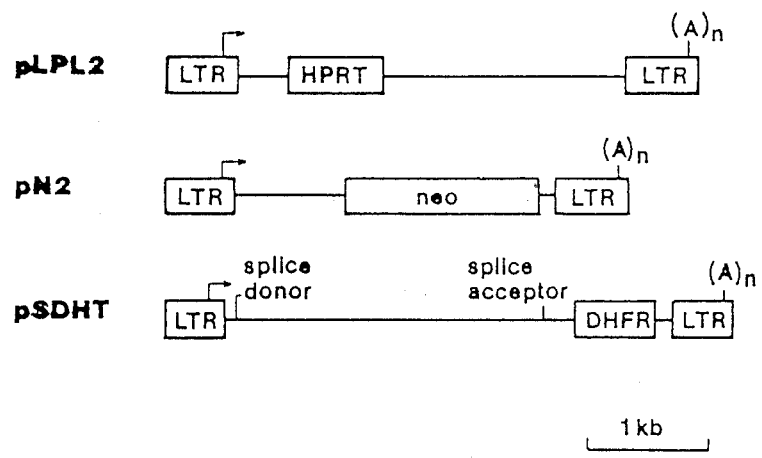
FIG. 4 depicts representative vectors carrying selectable markers as described in Examples 1 and 4.

Selectable markers in the vectors shown in FIG. 4 are expressed using transcriptional signals present in the viral LTRs. The Neo-virus pN2 (Nature 318: 149–154, 1985) and the DHFR-virus pSDHT (Somat.Cell.Mol.-Genet. 12: 175–183, 1986) have been described. The HPRT-virus pLPL2 is described below in Example 4.

For assay of virus carrying selectable markers, recipient cells were seeded at $5 \times 10^5$ per 60 mm dish on day one. On day two the medium was changed to medium containing 4 µg/ml polybrene, and aliquots of test virus were added. Unless otherwise indicated, virus was harvested by exposing culture medium to confluent dishes of virus-producing cells for 16 hours, removing the medium, and subjecting the medium to centrifugation at 3,000 g for 5 min. to remove cells and debris. On day three the cells were split 1:10 into selective medium: $10^{-7}$M methotrexate (Mtx) for DHFR-virus, 2 mg/ml G-418 (about 50% active) for Neo-virus, or HAT selective medium (30 µM hypoxanthine, 1 µM amethopterin, 20 µM thymidine) for HPRT-virus. Colonies were stained and counted on day nine.

EXAMPLE 2

Helper virus assay.

Helper virus was measured using the $S+L^-$ assay as described in Mol.Cell.Biol. 5: 431–437, 1985, hereby incorporated by reference. Briefly, the $S+L^-$ helper virus assay involves exposure of cat cells harboring a replication-defective transforming virus to test virus, followed by overlay of the cat cells with nontransformed rat NRK cells. The resence of helper virus in the test virus is indicated by focus formation in the otherwise flat NRK cells, due to rescue of the transforming virus followed by infection and transformation of the NRK cells.

EXAMPLE 3

Packaging constructs.

Representative packaging DNA constructs are depicted in FIG. 3 without surrounding plasmid sequences. Tall open boxes represent retroviral LTRs, short open boxes represent other retroviral sequences, and hatched boxes denote SV40 sequences. Landmark restriction sites are shown, but all of the sites for a given enzyme are not necessarily shown. Cis-acting features important for retrovirus replication are noted at the upper margin. Unless otherwise indicated, cleavage and ligation positions are designated in accordance with Van Beveren, C., et al., Nucleotide sequences complemented with functional and structural analysis, in R. Weiss, et al., (eds.), RNA Tumor Viruses, Vol. 2, pp. 766–782, Cold Spring Harbor Laboratory, Cold Spring Harbor, N.Y., 1985.

The plasmid containing a recombinant amphotropic helper virus (pAM) and the derivative of this virus in which the packaging signal has been removed (pPAM) have been described in Mol.Cell.Biol. 5: 431–437, 1985, hereby incorporated by reference. Briefly, the broadhost-range helper virus pAM was generated by replacing the env region of a DNA clone of MoMLV with the env region of amphotropic virus 4070A. Specifically, the env gene and part of the pol region of MoMLV DNA clone pMLV-K (J.Virol. 49: 214–222, 1984) were replaced with a SalI-to-ClaI fragment from amphotropic virus clone 4070A (J.Virol. 39: 777–791, 1981) to make pAM. The envelope glycoprotein encoded by the env gene is the primary determinant of retroviral host range. The amphotropic envelope glycoprotein can bind to cell surface receptors present on cells from a wide range of mammalian species. The major differences between MoMLV and virus 4070A are in the env region, and recombination points for insertion of the amphotropic env region were chosen in regions of relative homology. In addition, hybrid virus pAM retains the gag region of MoMLV, which determines N- and B-tropism (J.Virol. 48: 685–696, 1983). Amphotropic virus 4070A is N-tropic and is not able to infect BALB/c mouse cells. MoMLV is NB-tropic and can infect a wider range of mouse cell types, inluding BALB/c. Thus, the AM virus should have the broad-host-range characteristics of both MoMLV and amphotropic virus 4070A. Preliminary tests revealed that helper virus was generated from pAM following transfection into cells and that the virus had the predicted host range, in that it could infect both type N and type B mouse cells (a property of MoMLV) and could also infect and replicate in human and chicken cells (properties of amphotropic viruses).

Packaging vector pPAM was made by deleting from pAM the packaging signal for viral RNA, which has been shown to lie between the BalI and PstI sites at the 5' end of MoMLV (Cell 33: 153–159, 1983). Specifically, deletion was made of a BalI to PstI fragment spanning the packaging signal for the virus from MoMLV nucleotide positions 212 to 563. A PstI linker was ligated to the BalI site and then joined to the 5' PstI site after partial digestion of a molecule containing both PstI sites present in pAM.

The construct pPAM2 was made from pPAM by replacement of the 3' LTR with the late polyadenylation signal from SV40, isolated as a 237 bp BamHI to BclI fragment. The end of the retroviral genome was cleaved with RsaI at position 7762, which cuts just upstream of the termination codon of env, and a synthetic oligonucleotide was added to duplicate the part of env that was removed. This oligonucleotide also contained a BamHI site downstream of the terminator codon for env for addition of the SV40 fragment containing a polyadenylation signal.

pPAM3 was made from pPAM2 by removing viral sequences 5' of the viral enhancers in the 5' LTR by using a Sau3AI site at position −352.

pPAM4, in addition to the deletions made in pPAM3, has a deletion that removes the tRNA binding site and 3' portion of the 5' LTR, while preserving the splice donor site. This deletion was made by cleavage of the LTR at a SmaI site at position 28 in the R region of the LTR, addition of a BamHI linker, and linkage to a Sau3AI site at position 161 (BamHI and Sau3AI leave complementary 5' extensions).

The foregoing constructs are all carried in pBR322. pAM, pPAM, and pPAM2 are inserted in pBR322 in place of the Tet$^r$ gene between the ClaI and PvuII sites. The ClaI sites remain, but the sites at the other ends of the constructs were destroyed during attachment to the PvuII site of pBR322. pPAM3 and pPAM4 were inserted in place of the Tet$^r$ gene between BamHI and PvuII. Only the Sau3AI site remains at the 5' end of the latter two constucts, and the sites at the 3' end have been destroyed.

EXAMPLE 4

Generation and testing of packaging cell lines.

Clonal cell lines containing the packaging constructs were made by cotransfecting NIH/3T3 TK$^-$ cells, seeded the day before at $5 \times 10^5$/60 mm dish, with (i) 10 μg packaging construct DNA carried in pBR322 from Example 3, and (ii) 0.1 μg of the herpes simplex virus thymidine kinase (TK) gene carried as a BamHI fragment in pBR322 (Proc.Natl.Acad.Sci.USA 76: 3755–3759, 1979). Transfection was by the calcium phosphate precipitation procedure (Somat.Cell.Mol.-Genet. 7: 603–616, 1981; Virol. 52: 456–467, 1973). The cells were grown in HAT selective medium, and resultant TK$^+$ colonies were isolated using cloning rings.

Clones were screened for their ability to package a retroviral vector containing the selectable marker hypoxanthine-guanine phosphoribosyltransferase (HPRT) as follows. On day one, cells to be tested were seeded at $5 \times 10^5$ cells per 60 mm dish. On day two, the cells were transfected with 10 μg HPRT-virus plasmid pLPL2 (described below). On day three, the transfected cells were fed. On day four, medium from the transfected cells were removed, centrifuged at 3,000 g for 5 min. to remove cells and debris, and aliquots were analyzed for HPRT-virus using HPRT$^-$ rat 208F cells, and also for helper virus using the S+L$^-$ assay.

The HPRT-virus pLPL2 (see FIG. 4) is similar to the pLPL virus described previously (Proc.Natl.Acad.-Sci.USA 80: 4709–4713, 1983) but with two modifications. First, two GC-rich regions in the HPRT cDNA (Proc.Natl.Acad.Sci.USA 80: 477–481, 1983) that lie between the 5' LTR and the start codon of HPRT in pLPL were removed. NaeI was used to cut the HPRT cDNA 9 bp 5' of the start codon, a PstI linker was added, cleaved with PstI, and joined to the PstI site present in pLPL at the start of the HPRT cDNA. The second modification involved a deletion. pLPL contains, in addition to the normal retroviral packaging signal between the 5' LTR and HPRT, a second packaging signal lying downstream of the 3' LTR. This second signal might allow packaging of RNAs initiating in the 3' LTR and extending into pBR322 sequences following transfection of pLPL into packaging cell lines. To avoid this possibility, the second signal was removed by cleavage at a BalI site just 3' of the 3' LTR, and an EcoRI to BalI fragment containing the HPRT-virus was inserted in place of the Tet$^r$ gene of pBR322 between the EcoRI and PvuII sites. HPRT-virus production following transfection of pLPL2 into packaging cells was about 3-fold higher than for pLPL.

In addition to the described Ca-phosphate mediated technique, other transfection protocols for introducing nucleic acid sequences into cells can be employed in the practice of this invention. DEAE-dextran mediated transfection techniques, lysozyme fusion or erythrocyte fusion, osmotic or sucrose shock, scraping, or direct uptake by the cells from their surroundings. The above illustrative transfection techniques can be augmented by subjecting the cells to electric currents. The vectors can also be microinjected directly or indirectly via erythrocyte-mediated microinjection techniques, into a cell.

EXAMPLE 5

Cocultivation assay for packaging function transfer.

NIH/3T3 cells nonproductively infected with the pN2 Neo-virus (NIH/3T3-N2 cells) were made by infecting NIH/3T3 cells with helper-free N2 virus from PA317-N2 cells (see below). AM-MLV helper virus [pAM?] infection of clonal NIH/3T3-N2 cell lines resulted in production of $10^6$–$10^7$ Neo-virus per ml of medium exposed to the cells, showing that the Neo-virus can be efficiently rescued.

Figure 5:
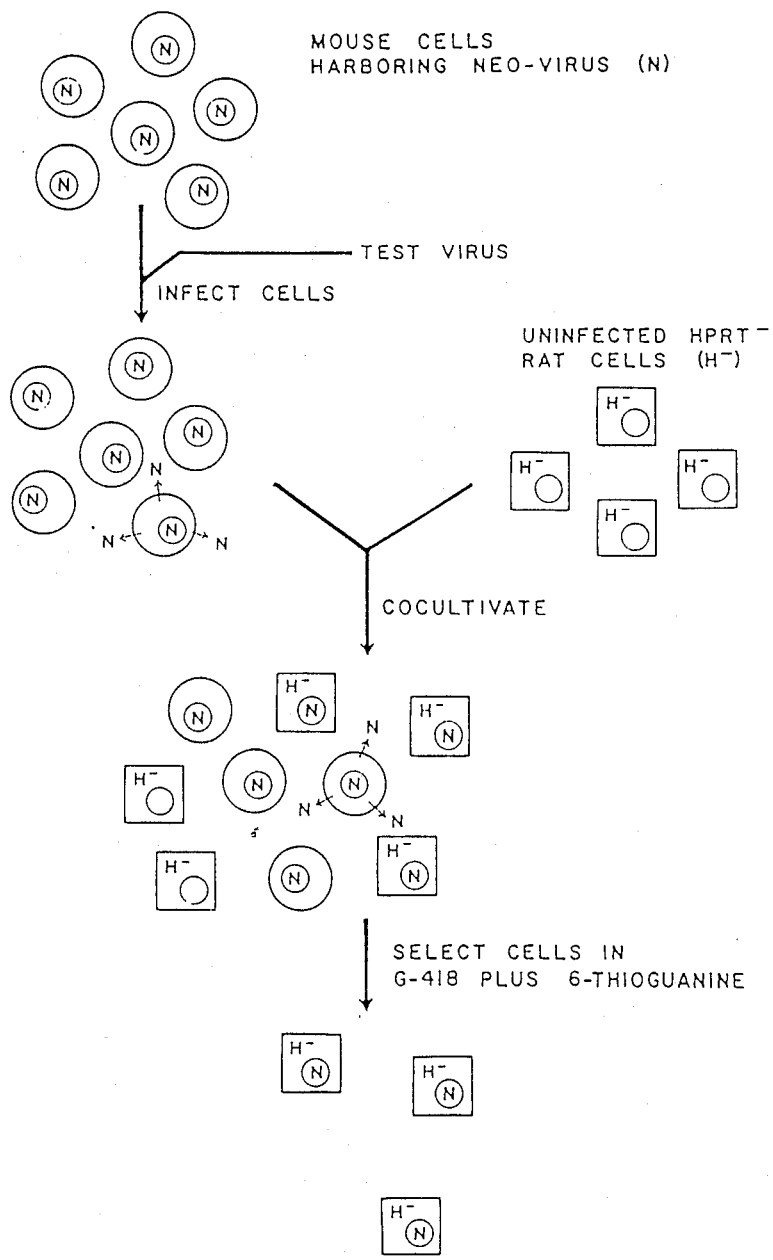
FIG. 5 is a diagrammatic outline of an assay for packaging system transfer as described in Example 5.

We designed the experiment depicted in FIG. 5 as a sensitive assay for detection of packaging function transfer. First, NIH/3T3 (TK$^-$) cells harboring but not producing a Neo-virus (NIH/3T3-N2 cells) were exposed to medium harvested from various packaging cells. Cell lines to be tested for production of virions containing the packaging system were seeded at $10^6$ cells per 60 mm dish on day one. One day two, NIH/3T3-N2 cells were separately seeded at $10^5$/60 mm dish, and the test cells were fed. In the morning of day three, 12 hours after the test cells had been fed, medium from the test cells was removed and centrifuged at 3,000 g for 5 min. to remove cells and debris, and the NIH/3T3-N2 cells are infected with 1 ml aliquots in the presence of 4 μg/ml polybrene. The test cells were fed, and the NIH/3T3-N2 cells were again infected 12 hours later. If the NIH/3T3 cells became infjected by virus resulting in transfer to the packaging function, they would begin to secrete Neo-virus.

We next mixed the infected NIH/3T3-N2 cells with rat HPRT$^-$ fibroblasts, cocultivated the cells for 4 days, and assayed the mixed populations for the presence of HPRT$^-$, Neo-virus infected rat cells by exposing the cells to G-418 and 6-thioguanine and scoring resistant colonies. Specifically, the infected NIH/3T3-N2 cells were fed on day four, and on day five were trypsinized, divided into two aliquots and added to 60 mm dishes containing $8 \times 10^5$ 208F cells each. On day six, the cocultivated cells were confluent, and were trypsinized and divided 1:10. On day nine, after four days of cocultivation, the cells were split 1:10 into 100 mm dishes in medium containing 2 mg/ml G-148 and 20 M 6-thioguanine. Cells were fed with selective medium every 3 days, and colonies were stained and counted on day fourteen. NIH/3T3-N2 cells die in medium containing 6-thioguanine, and 208F cells die in G-418, so that only cells that survive are 208F cells infected with Neo-virus rescued from the NIH/3T3-N2 cells.

The reason for the cocultivation step in this assay is that small amounts of virus produced by a few NIH/3T3-N2 cells cannot be detected in medium exposed to the cells (data not shown), presumably because the virus binds rapidly to cells in the dish which are not producing virus and thus have available viral receptors. Cocultivation of the NIH/3T3-N2 cells with the rat cells allows transfer to occur directly between cells, and therefore increases the sensitivity of the assay.

EXAMPLE 6

Retrovirus packaging cell lines.

Following the procedures set forth in Example 4, we introduced the DNA constructs depicted in FIG. 3 into NIH/3T3 TK$^-$ cells by cotransfection using the TK gene as a selectable marker. TK$^+$ colonies were isolated and screened for production of replication-competent virus using the S$^+$L$^-$ assay, and for their ability to package a standard retrovirus vector containing HPRT. We were unable to detect helper virus production from any of the clones analyzed (>70 clones) by using the S$^+$L$^-$ assay, with a limit of sensitivity of 1 virus/ml. As shown in Table 1, greater than 50% of the clonal cell lines made with any one of the packaging constructs were able to package the HPRT-virus, suggesting that rearrangement of the transfected DNA was not required in order to obtain such lines.

TABLE 1

Ability of clonal cell lines cotransfected with packaging constructs to package a retroviral vector.

| Packaging construct | Highest virus titer(cfu/ml) | % of clones producing >20% of maximum titer | % of clones producing no virus(<10 cfu/ml) | Name of best clone |
|---|---|---|---|---|
| pPAM | $3 \times 10^4$ | 50% | 13% | PA12 |
| pPAM2 | $6 \times 10^4$ | 40% | 40% | PA212 |
| pPAM3 | $6 \times 10^4$ | 40% | 29% | PA317 |
| pPAM4 | $4 \times 10^3$ | 25% | 50% | PA405 |

The Table 1 data derives from two separate transfections, with at least eight clones screened from each transfection. Roughly equivalent virus titers (expressed in colony forming units per ml of medium, or cfu/ml) were obtained from cell lines containing pPAM, pPAM2, and pPAM3. However, cell lines made with pPAM4 were about 10-fold less efficient in packaging the HPRT-virus.

Since virus titer is critical for many applications of retroviral vectors, we used the best pPAM3 transfectant, named PA317, in further studies instead of the best pPAM4 transfectant, PA405. The deletions made in pPAM3 are considered sufficient to severely reduce packaging of RNA derived from this construct into virions, and even if the RNA is packaged, provirus formation in infected cells should be blocked at both the level of reverse transcription of the RNA to DNA, and at the level of virius integration into the host genome.

EXAMPLE 7

Comparison of virus titer from vector infected packaging cell lines.

Table 1 shows that the titer of virus produced transiently following transfection of PA12 or PA317 cells with the HPRT-virus was similar, indicating that PA317 cells efficiently package retrovirus vectors, as do PA12 cells. To further test the PA317 line, we infected PA317 cells with a virus containing a dominant-acting selectable DHFR gene and assayed individual infected clones for production of DHFR-virus, and compared these results to those obtained using PA12 cells. The comparative test results are shown in Table 2.

TABLE 2

Virus productions from packaging cells containing the SDHT DHFR-virus.

| Packaging cell line | DHFR-virus infected cell clone | DHFR-virus titer (cfu/ml) | Helper titer (ffu/ml) | DHFR-virus titer after helper virus infection (cfu/ml) |
|---|---|---|---|---|
| PA12 | 1 | $2 \times 10^6$ | <1 | |
| | 2 | $2 \times 10^6$ | <1 | |
| | 3 | $2 \times 10^3$ | N.D.* | |
| | 4 | $1 \times 10^4$ | N.D. | |
| | 5 | $4 \times 10^4$ | N.D. | |
| | 6 | $4 \times 10^6$ | <1 | |
| PA317 | 1 | $6 \times 10^5$ | <1 | $6 \times 10^6$ |
| | 2 | $6 \times 10^5$ | <1 | $4 \times 10^6$ |
| | 3 | $1 \times 10^7$ | <1 | $3 \times 10^7$ |
| | 4 | $4 \times 10^6$ | <1 | |
| | 6 | $3 \times 10^5$ | <1 | $6 \times 10^6$ |
| | 7 | $<1 \times 10^3$ | <1 | $4 \times 10^7$ |
| | 8 | $5 \times 10^6$ | <1 | |
| | 9 | $1 \times 10^5$ | <1 | $10^6$ |

*not determined

Packaging cell lines containing retroviral vectors were made by transfecting Psi-2 cells followed by harvest of virus two days later and infection of amphotropic packaging cell lines as previously described (17). Independent vector infected cell lines were isolated following drug selection by using cloning rings. As shown in Table 2, the DHFR-virus titer produced from DHFR-virus infected PA317 clones was very high, up to $10^7$ DHFR-virus per ml of medium, with no detectable helper virus. The PA317 clones on average produced slightly higher-titer DHFR-virus than the PA12 clones, and the best clone was slightly better than the best PA12 clone. We conclude that the additional mutations present in the packaging DNA in PA317 cells do not adversely affect its ability to make high-titer vector producing cell lines.

EXAMPLE 8

Inhibition of recombination to produce helper virus.

We have previously shown that certain vectors interact with the PA12 cell line to produce helper virus; Somat.Cell.Mol.Genet. 12: 175–183, 1986, hereby incorporated by reference. The N2 virus (FIG. 4), as well as derivatives containing additional genes inserted at the 3' end of the virus, produce helper virus when introduced into PA12 1 cells. Helper virus production is dependent upon the presence of gag sequences upstream of the neo gene in this vector, as we have shown that deletion of these sequences leads to vectors that do not produce helper virus. A plausible model for this event would involve copackaging of the viral vector and RNA derived from the pPAM packaging construct present in PA12 cells, followed by recombination in the gag region during reverse transcription in an infected cell. Addition of the 5' portion of the vector to the packaging construct would result in creation on a fully replication-competent virus containing a vector-derived packaging signal. In contrast, two recombination events would be required to generate helper virus from the pPAM3 packaging construct, since defects are present at both ends of pPAM3. A double recombination event is presumably quite rare, and so we predicted that it might be possible to generate helper-free virus by introduction of the N2 vector into PA317 cells. This prediction was confirmed in the following experiment.

The N2 virus was introduced (as described above) into PA12 or PA317 retrovirus packaging cells, and independent clones containing the virus were isolated and screened for the production of Neo-virus and helper virus. Helper virus production from PA317 cells containing the N2 virus was not detected, whereas production from PA12 cells containing the N2 virus was always detected. Representative comparative test results are presented in Table 3.

TABLE 3

Virus production from packaging cells containing the N2 Neo-virus.

| Packaging cell line | N2-virus infected cell clone | Neo-virus titer (cfu/ml) | Helper titer (ffu/ml) | Neo-virus titer after helper virus infection (cfu/ml) |
|---|---|---|---|---|
| PA12 | 1 | $5 \times 10^6$ | 20 | |
| | 2 | $4 \times 10^6$ | <1 | |
| | 3 | $2 \times 10^7$ | 40 | |
| | 4 | $1 \times 10^7$ | 190 | |
| | 5 | $5 \times 10^6$ | 200 | |
| PA317 | 1 | $8 \times 10^6$ | <1 | $2 \times 10^7$ |
| | 2 | $1 \times 10^6$ | <1 | |
| | 3 | $2 \times 10^3$ | <1 | $3 \times 10^7$ |
| | 4 | $4 \times 10^6$ | <1 | |
| | 5 | $2 \times 10^6$ | <1 | |
| | 6 | $1 \times 10^5$ | <1 | $4 \times 10^7$ |
| | 7 | $4 \times 10^5$ | <1 | $1 \times 10^7$ |
| | 8 | $6 \times 10^5$ | <1 | |
| | 10 | $2 \times 10^5$ | <1 | |
| | 11 | $1 \times 10^7$ | <1 | |
| | population* | $6 \times 10^6$ | <1 | |

*a population of over 100 independent clones was analyzed to check for rare events leading to helper virus production.

Table 3 shows that all of the PA12-N2 clones produced Neo-virus, and all but one (clone #2) produced helper virus. Helper virus production by this #2 clone was detected after further passage of the cells. The entire experiment was repeated with a similar result.

Most of the PA317-N2 clones likewise produced Neo-virus but, in contrast, none of these pPAM3-transformed clones produced helper virus. Passage of two of the high titer Neo-virus producing PA317-N2 cell lines for over one month did not result in helper virus production, as measured by the S+L− assay. In addition, NIH/3T3 cells infected with 1 ml aliquots of virus from these lines did not produce helper virus or Neo-virus when assayed more than two weeks after infection.

EXAMPLE 9

Virus production from Psi-2 cells containing the N2 Neo-virus.

Recent reports indicate that when the N2 virus was transfected into Psi-2 cells, helper virus production from clonal cell lines was not detected. Science 230: 1395–1398, 1985; Nature 318: 149–154, 1985. Psi-2 cells contain a packaging construct which is similar to PA12 cells, except that the envelope regions are from murine viruses with different host range. Thus, we predicted that Psi-2 cells would interact with the N2 virus to generate helper virus in a fashion analogous to PA12 cells. We tested for production of helper virus from Psi-2 cells after introduction of the N2 virus by using the XC helper virus assay described in Virology 42: 1136–1139, 1970. This assay is used for detection of Mo-MLV, the virus on which the Psi-2 line is based. The results are shown in Table 4. In addition to isolating clonal cell lines (#1–6) containing the N2 virus, we analyzed cell populations (A-D) containing many independent clones so that a rare event resulting in helper virus production might be detected. Populations A and B were derived by transfection of Psi-2 cells with pN2 without cloning the resulting colonies. Cell populations C and D were derived by transfecting Psi-2 cells with helper-free virus from the cell line PA317-N2 c11 (Table 3).

TABLE 4

Virus production from Psi-2 cells containing the N2 Neo-virus.

| N-2 virus transfected Psi-2 cell clone | Neo-virus titer (cfu/ml) | Helper titer (ffu/ml) |
| --- | --- | --- |
| 1 | $2 \times 10^4$ | $<1$ |
| 2 | $9 \times 10^4$ | $<1$ |
| 3 | $8 \times 10^5$ | $10^2$ |
| 4 | $4 \times 10^5$ | $>10^3$ |
| 5 | $2 \times 10^4$ | $>10^3$ |
| 6 | $3 \times 10^5$ | $<1$ |
| population A | $>10^4$ | $2 \times 10^2$ |
| population B | $>10^4$ | 8 |
| population C | $>10^4$ | $5 \times 10^2$ |
| population D | $>10^4$ | $>10^5$ |

As shown in Table 4, all of the populations of Psi-2 cells containing the N2 virus secreted helper virus in addition to N2 virus. In addition, three of the six clonal N2 transfected Psi-2 cell lines secreted helper virus in addition to N2 virus. The level of helper virus secretion was highly variable among the cells analyzed here, which may reflect a relatively infrequent event which generates helper virus followed by slow spread of helper virus in the cells. We conclude that even though it is possible to isolate clones of N2 virus containing Psi-2 cells which apparently do not secrete helper virus, production of helper virus is a frequent event. In contrast, we have not detected helper virus production from Psi-2 cells not containing vectors.

EXAMPLE 10

Analysis of packaging clones that produce low titer virus.

Some of the PA317 cell clones infected with selectable vectors produced low titer virus, e.g., PA317-DHFR c7 (Table 2) and PA317-N2 c3 (Table 3). The explanation for this might be that the integrated virus suffered mutations so that it could not efficiently replicate, or that PA317 cells are heterogeneous in their ability to express virus packaging functions. To answer this question, we infected several PA317-SDHT and PA317-N2 clones with AM-MLV helper virus, passaged the cells for over 2 weeks to allow the helper virus to spread, and assayed the clones for production of virus. After infection, all clones analyzed produced high vector titers, showing that the SDHT or N2 vectors were not defective. We therefore conclude that there is heterogeneity in the packaging ability of PA317 cells, possibly because of loss of the transfected pPAM3 DNA that is required for retrovirus vector packaging.

EXAMPLE 11

Sensitive assay for helper virus production.

We next increased the sensitivity of the $S^+L^-$ assay described in Example 2, in an attempt to detect helper virus production from the PA12 or PA317 cell lines. In many experiments performed in this lab we have never seen helper virus production from PA12 cells as measured by the $S^+L^-$ assay. We have detected helper virus production from retrovirus vector containing cells only in the case of the N2 Neo-virus and its derivatives. However, increasing the sensitivity of the assay might result in helper detection, or detection of a rare event involving transfer of the packaging function.

In order to increase the sensitivity of the assay, we repeatedly exposed the cat cells at 12-hour intervals to large quantities of medium harvested from cells to be tested for helper virus production, and then cocultivated the cat cells with NRK cells. The assay was performed using PA12 and PA317 cells, and DHFR- virus producing PA12 and PA317 cells (PA12-SDHT c6 and PA317-SDHT c3, Table 2). No foci were induced by any of these cell lines, and thus we were unable to detect helper virus production by these lines ($<0.1$ helper virus/ml) (data not shown). In contrast, AM-MLV helper virus harvested from AM-MLV virus producing NIH/3T3 TK$^-$ cells induced $3 \times 10^6$ foci per ml of medium. In addition, critical observation did not reveal any differences between the test plates and a mock infected control dish. Thus there was no indication in this assay of transfer of the packaging function.

EXAMPLE 12

Detection of packaging function transfer.

Using the cocultivation assay described in Example 5, we found that medium from Psi-2 cells consistently induced low level Neo-virus release from NIH/3T3-N2 cells (Table 4). Medium from PA12 cells or PA12 cells producing DHFR-virus also induced Neo-virus release, but at even lower levels. We did not detect colony production using medium from PA317 cells or from DHFR-virus producing PA317 cells.

TABLE 5

Detection of Neo-virus rescue from cells following infection with medium exposed to packaging cell lines.

| | Colonies Induced | |
| --- | --- | --- |
| Test cells | Expt. 1 | Expt. 2 |
| NIH/3T3(TK$^-$) | 0 | 0 |
| Psi-2 | 18 | 10 |
| PA12 | 3 | 2 |
| PA12-SDHT | 0 | 1 |
| PA317 | 0 | 0 |
| PA317-SDHT | 0 | 0 |

We can rule out endogenous mouse viruses as being responsible for Neo-virus rescue in these experiments because these viral genomes are present in all of the packaging lines, while not all can induce Neo-virus production. Retroviruses can induce cell fusion, but colony formation as a result of cell fusion can be ruled out because fusion products between the HPRT$^-$ rat and G-418 resistant mouse cells would still be sensitive to 6-thioguanine, since the mouse cells are HPRT$^+$. In addition, we rule out colony formation as a result of cell fusion because virus from the packaging cell lines should induce fusion at similar rates, and some lines do not induce colony formation. We conclude that deletion of the packaging signal is not sufficient to prevent transfer of the packaging function. However, additional alterations in the packaging system in PA317 cells reduce packaging function transfer to undetectable levels.

While the present invention has been described in conjunction with a preferred embodiment and illustrative examples, one of ordinary skill after reading the foregoing specification will be able to effect various changes, substitutions of equivalents, and alterations to the compositions and methods set forth herein. It is therefore intended that the protection granted by Letters Patent hereon be limited only by the definitions contained in the appended claims and equivalents thereof.

The embodiments of the invention in which an exclusive property or privilege is claimed are defined as follows:

1. An improved DNA construct useful for making retrovirus packaging cell lines comprising an amphotropic retroviral gene sequence derived from murine leukemia virus encoding in trans all virion proteins required for packaging a replication-incompetent retroviral vector and characterized by its ability, when transferred into susceptible host cells, to produce virion proteins capable of packaging said replication-incompetent retroviral vector at high titer, without the production of replication-competent helper virus, which vector contains a heterologous gene, said retroviral gene sequence lacking a packaging signal, a site for translocation of reverse transcriptase during first strand DNA synthesis, a site for initiation of second strand DNA synthesis and a proviral integration signal.

2. The improved DNA construct of claim 1, wherein the retroviral gene sequence encodes gag and pol proteins, and further encodes env proteins having an amphotropic host range.

3. Cells transfected by the DNA construct of claim 1.

4. A DNA construct having the characteristics of pPAM3 (ATCC No. 40234).

5. A process for constructing an improved DNA construct useful for making retrovirus packaging cell lines, comprising deleting from the genome of a replication-competent amphotropic retrovirus derived from murine leukemia virus, the packaging signal, the site of initiation of second strand DNA synthesis, the site required for translocation of reverse transcriptase during first strand DNA synthesis, and the provirus integration signal.

6. A DNA molecule constructed according to the process of claim 5.

7. A process for constructing a retrovirus packaging cell line comprising the steps of:
 introducing into cells an improved DNA construct comprising an amphotropic retroviral gene sequence derived from murine leukemia virus encoding in trans all virion proteins required for packaging a replication-incompetent retroviral vector and lacking a packaging signal, the site for initiation of second strand DNA synthesis, the site required for translocation of reverse transcriptase during first strand DNA synthesis, and the provirus integration signal; and
 screening for cells containing said construct and producing said virion proteins.

8. The process of claim 7 further comprising the step of cotransfecting the cells with a selectable marker sequence.

9. A cell line produced by the process of claim 7.

10. A packaging cell line comprising a DNA construct having an amphotropic retroviral gene sequence derived from murine leukemia virus encoding in trans all virion proteins required for packaging a replication-incompetent retroviral vector and lacking a packaging signal, a site for translocation of reverse transcriptase during first strand DNA synthesis, a site for initiation of second strand DNA synthesis and a proviral integration signal, and packaging cell line being capable of packaging said replication-incompetent retroviral vector at high titer, without the production of replication-competent helper virus.

11. A cell line having the characteristics of PA317 (ATCC No. CRL 9078).

* * * * *

UNITED STATES PATENT AND TRADEMARK OFFICE
CERTIFICATE OF CORRECTION

PATENT NO. : 4,861,719

DATED : August 29, 1989

INVENTOR(S) : A.D. Miller

Page 1 of 2

It is certified that error appears in the above-identified patent and that said Letters Patent is hereby corrected as shown below:

| Column | Line | Error |
|---|---|---|
| Abstract | 19 | "CLR" should be --CRL-- |
| 1 | 8 | "the" should be --this |
| 2 | 41 | after "6349-6353" add --, 1984--. |
| 3 | 53 | "CRL9078)" should be --CRL 9078)-- |
| 4 | 58 | after "5'" (first occurrence) add --end-- |
| 4 | 68 | "delected" should be --deleted-- |
| 5 | 16 | "retroviris-like" should --retrovisus-like--. |
| 5 | 20 | "a" should be --as-- |
| 5 | 56 | insert a "." (period) after "range" |
| 6 | 41 | "resence" should be --presence-- |
| 7 | 6 | "SalI-to-ClaI" should be --SalI-to-ClaI-- |
| 7 | 21 | "inluding" should be --including-- |
| 7 | 33 | "PStI" should be --PstI-- |
| 8 | 3 | "constucts" should be --constructs-- |
| 8 | 28 | "were removed" should be --was removed-- |
| 9 | 8 | "[pAM?]" should be --[pAM]-- |
| 9 | 19 | "One" should be --On-- |
| 9 | 33 | "In" should be --On-- |
| 9 | 37 | "are" should be --were-- |
| 9 | 41 | "infjected" should be --infected-- |
| 9 | 59 | "that" should be --the-- |
| 10 | 53 | "virius" should be --virus-- |
| 11 (Table 2) | 2 | "productions" should be --production-- |
| 11 | 49 | "PA12 1" should be --PA12-- |
| 11 | 59 | "on" should be --of-- |
| 15 (Claim 5, line 5) | 35 | "of" should be --for-- |

UNITED STATES PATENT AND TRADEMARK OFFICE
CERTIFICATE OF CORRECTION

PATENT NO. : 4,861,719

DATED : August 29, 1989

INVENTOR(S) : A.D. Miller

It is certified that error appears in the above-identified patent and that said Letters Patent is hereby corrected as shown below:

<u>Column</u>  Line 16    31    "and" should be --said--.

(Claim 10, line 9)

Signed and Sealed this

Ninth Day of October, 1990

Attest:

HARRY F. MANBECK, JR.

Attesting Officer

Commissioner of Patents and Trademarks